United States Patent [19]

Binder

[11] 4,368,740
[45] Jan. 18, 1983

[54] PHYSIOLOGIC ANALYZER

[76] Inventor: Andy S. Binder, 1487 Crestline Dr., Santa Barbara, Calif.

[21] Appl. No.: 203,355

[22] Filed: Nov. 3, 1980

[51] Int. Cl.$^3$ ............................................... A61B 5/08
[52] U.S. Cl. ................................... 128/718; 128/719; 128/725
[58] Field of Search ................ 128/716, 718, 719, 725

[56] References Cited

U.S. PATENT DOCUMENTS

| | | | |
|---|---|---|---|
| 3,523,529 | 8/1970 | Kissen | 128/718 |
| 3,799,149 | 3/1974 | Rummel et al. | |
| 3,834,375 | 9/1974 | Sanctuary et al. | 128/719 |
| 3,895,630 | 7/1975 | Bachman | |
| 4,112,491 | 9/1978 | Bugay | |
| 4,197,857 | 4/1980 | Osborn | 128/718 |

OTHER PUBLICATIONS

Talbot et al., Conference Advances in Bioeng., Winter Ann. Meeting of Amer. Soc. of Mech. Eng., N.Y., 1979, pp. 23-25.
Howard et al., Computerized Cardiopulmonary Stress Testing in Children, IEEE, 1979.
Wessel et al., IEEE Conf.: Computers in Cardiology, Stanford, Ca., Sep. 1978, pp. 97-104.
Michels et al., Conf.: Eng. in Med. and Bio., L.A., Nov. 1977, p. 19.
Publication entitled Techniques, Equipment, 13 through 34.
Article from Journal of Applied Physiology, vol. 38, No. 5, May 1975, Entitled Breath-by-Breath Analysis of Ventilation and Pulmonary Gas Exchange by Digital Computer.
Acta Physiologica Scandinavica Supplementum 415, from the Departments of Aviation and Naval Medicine, entitled Dynamics of Pulmonary Gas Exchange and Heart Rate Changes at Start and End of Exercise, by Linnarsson.

*Primary Examiner*—Kyle L. Howell
*Assistant Examiner*—John C. Hanley
*Attorney, Agent, or Firm*—Manfred M. Warren; Robert B. Chickering; Glen R. Grunewald

[57] ABSTRACT

A physiologic analyzer is disclosed for continuous measurement of a subject's metabolic functions in which signals from ventilatory flow rate sensors and gas analyzers are processed to provide continuous measurement of the subject's ventilatory volume, carbon dioxide production, oxygen consumption, respiratory exchange ratio, and other metabolic functions of interest. An expiratory oxygen concentration sampler is enabled only when oxygen concentration deviates from the inspired value. When enabled, the sampler provides at its output a series of discrete signals proportional to successive instantaneous values of oxygen concentration in expired breath. A similar sampler is used in the processing of the carbon dioxide concentration signals. A respiratory cycle timer measures elapsed time between successive inspirations and provides a breath duration signal which is used for rate computations. Interpretation and analysis of test results is greatly facilitated by displaying all metabolic measurements as a function of oxygen consumption.

11 Claims, 5 Drawing Figures

PHYSIOLOGIC ANALYZER

BACKGROUND OF THE INVENTION

1. Field of the Invention

This invention relates to systems for the measurement of metabolic functions and more particularly systems measuring ventilation and pulmonary gas exchange.

2. Description of the Prior Art

It has long been known that analysis of a person's respiratory air provides valuable information relating to the condition of the subject's pulmonary system. The four most commonly measured variables are respiratory volume, oxygen consumption, carbon dioxide production, and respiratory exchange ratio, which is the ratio of carbon dioxide produced to oxygen consumed. Earlier efforts directed towards respiratory gas analysis involve the timed collection of expired breath in rubberized breathing bags, measuring the volume collected, and analyzing the gas composition contained within. Metabolic rates were then calculated from the data obtained. Needless to say, this method was time consuming, subject to great error, and could be performed only by well equipped laboratories. Furthermore, the aforementioned method was not well suited to the measurement of short duration transients in metabolic functions.

Since the data obtained from respiratory gas analysis is so valuable in diagnosing cardiopulmonary dysfunctions and evaluating overall cardiovascular condition, intensive effort has been directed towards automated systems. The intense nationwide interest in running and in physical conditioning in general has sparked further inventive effort in this field. Analysis of ventilation and pulmonary gas exchange provides an objective means for evaluating the effectiveness of various exercise regimes. Improvements and reduction in the size of gas analyzers and digital computers have resulted in the appearance of a number of automated ventilation and pulmonary gas exchange analyzers. These devices range from complicated laboratory systems requiring the use of powerful computers to simpler, less versatile systems for clinical use. Notably lacking in the prior art are systems which meaningfully integrate cardiac and pulmonary data. Since a subject's cardiovascular and pulmonary systems do not function independently, there is a need for testing devices which analyze variables relating to both and which can display the results in a manner which readily yields usable information.

Given the state of the art in gas analyzers and microprocessors, it is a reasonably simple task to construct a metabolic analyzer capable of measuring ventilation volume, carbon dioxide production, oxygen consumption, and respiratory exchange ratio. The simplest system would be merely an updated, automated version of the earliest breathing bag systems previously described. If one is interested only in long-term averaged values for metabolic functions, no particularly difficult technical problems are presented. When one is interested, however, in the transient behavior of ventilatory and metabolic responses, the technical demands are much greater. When one is interested in short interval measurement of metabolic variables, time delays and asynchronicities which are ignored in long-term averaged measurements take on a great significance. The signals from ventilatory flow sensors and gas concentration analyzers represent physiologic variables which are, in reality, synchronized. Delays introduced by sensor response lags, plumbing and the like, can cause great error in the calculation of transient metabolic phenomena. Various hardware schemes for correcting these errors have been proposed so that accurate short-term metabolic analysis can be made.

A common solution is to employ a wideband magnetic recorder to record the various signals as they are produced. The recording can then be played back and the various asynchronous signals aligned for further processing. A similar scheme digitizes signals before storage on a magnetic medium. The complexity and cost of the aforementioned solutions to the time delay problems greatly limit their applicability outside of the research laboratory.

A less complicated solution, disclosed in the prior art, utilizes a combination of analog and digital delay circuits in conjunction with the analog computer to effect time alignment of flow and concentration signals. The time delay introduced in the flow signal in this system is of a fixed duration which must be experimentally derived. Any changes in the physical dimensions of the system or substitution of any components would certainly change the proper time delay value, thus necessitating complete recalibration. The instant invention discloses a simple and elegant means for the time alignment of flow and concentration signals which allows fast and accurate measurement of physiologic transients. In this system there are no fixed time delays nor is there any need for wideband analog magnetic recorders or their digital equivalent.

SUMMARY OF THE INVENTION

It is the object of this invention to provide a simple system which overcomes the problems referred to above. The device of the instant invention allows sophisticated and accurate measurement and analysis of short-term ventilatory and metabolic phenomena. By eliminating the need for wideband signal recording and by not employing fixed time delays, the complexity of the system is greatly reduced while the accuracy and flexibility are enhanced.

The instant invention employs a bidirectional flow transducer (pneumotachygraph) to measure the flow rate of inspired and expired breath. Oxygen and carbon dioxide analyzers are employed to measure the concentrations of these gases in inspired and expired breath. Concentration and flow signals are effectively synchronized through the use of activity detectors which control flow integrators and gas concentration samplers. The inspiratory flow integrator is controlled by its respective activity detector which enables the flow integrator upon the initiation of inspiratory flow and resets the integrator upon the completion of inspiratory flow. A storage register samples and stores successive values of integrated flow signals to provide a series of discrete values corresponding to successive values of inspiratory volume. An expiratory flow integrator is similarly controlled by its own activity detector which enables the integrator upon the initiation of expiratory flow and resets it at completion. A storage register samples and stores successive values of integrated expiratory flow which correspond to successive values of expiratory volume. The output signal from the oxygen analyzer is offset so that only deviations from oxygen concentration in the inspired gas will appear at the input of the oxygen sampler. The oxygen sampler is controlled by an activity detector which enables the sampler when oxygen concentration decreases from that concentration present in inspired gas and resets the sampler upon detecting oxygen concentration greater than or equal to the inspired concentration. The sampling rate of the oxygen sampler is identical to that of the storage registers which sample and store discrete values of integrated flow information.

The output from the carbon dioxide analyzer is similarly offset so that only deviations from the inspired carbon dioxide concentration will appear at the input of the carbon dioxide sampler. The carbon dioxide sampler is controlled by its activity detector which enables the sampler upon the detection of carbon dioxide concentrations greater than inspired values. Resetting of the sampler occurs upon the detection, by the activity detector, of carbon dioxide concentrations less than or equal to inspired values. The carbon dioxide sampler operates at the same sampling rate as the oxygen sampler and the two storage registers which sample and store successive discrete values of inspiratory and expiratory volume. As a result of this unique configuration of samplers and integrators, each controlled by its own activity detector, a series of discrete volume signals and a series of discrete gas concentration signals are obtained for each breath, these series corresponding to each other in that the first value sampled by the oxygen sampler corresponds to the first carbon dioxide sample and the first sampled value of expiratory volume present in the storage register. Even though these samples are obtained at slightly different times, owing to response lags, etc., once obtained they can be multiplied, divided, and otherwise computationally processed as synchronized signals.

Since the initiation of integration and sampling is controlled by the detection of physiologic events rather than by fixed timers, the system is self-synchronizing and its accuracy will not be affected by any of the myriad of factors which affect the accuracy of systems which employ fixed time delays.

An inspiratory cycle timer is employed which measures the time interval between successive enablings of the inspiratory flow integrator, and this inspiratory cycle time is used in the computation of the respiratory rate and the rate of oxygen consumption and carbon dioxide production. Additional system structures allow for the measurement of other ventilatory data of interest, such as peak inspiratory and expiratory flow and end tidal oxygen and carbon dioxide concentrations. The system allows for simple continuous measurement of oxygen consumption, not only during normal air breathing, but also during conditions of pure oxygen breathing. Data from a cardiotachometer and oximeter can be integrated into the system and processed so as to provide meaningful data in a readily usable format which graphs all the variables against oxygen consumption.

DETAILED DESCRIPTION OF THE INVENTION

Figure 1:
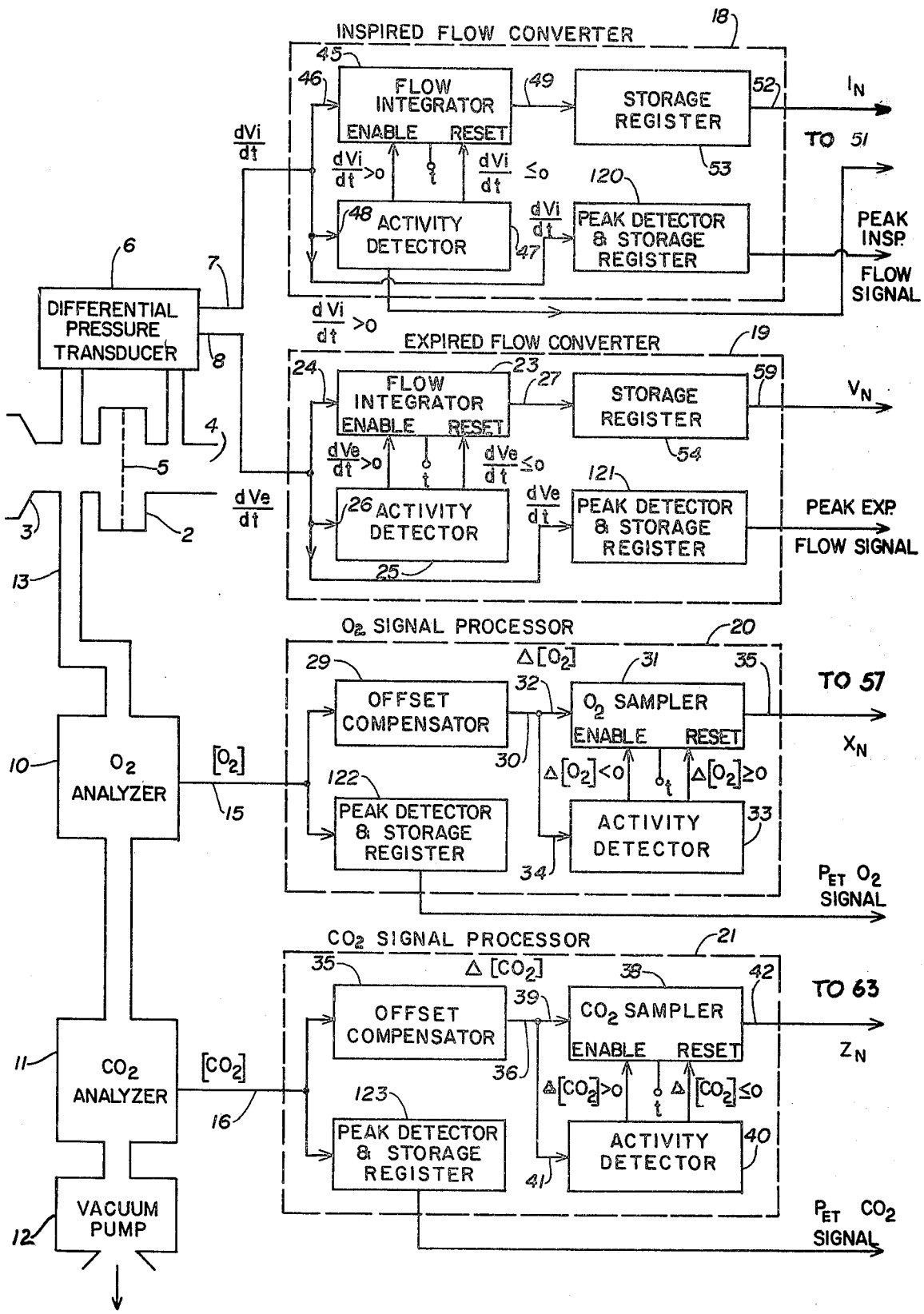
FIG. 1 is a block diagram of the breath-handling portions of the system, together with the associated signal processors.
Figure 2:
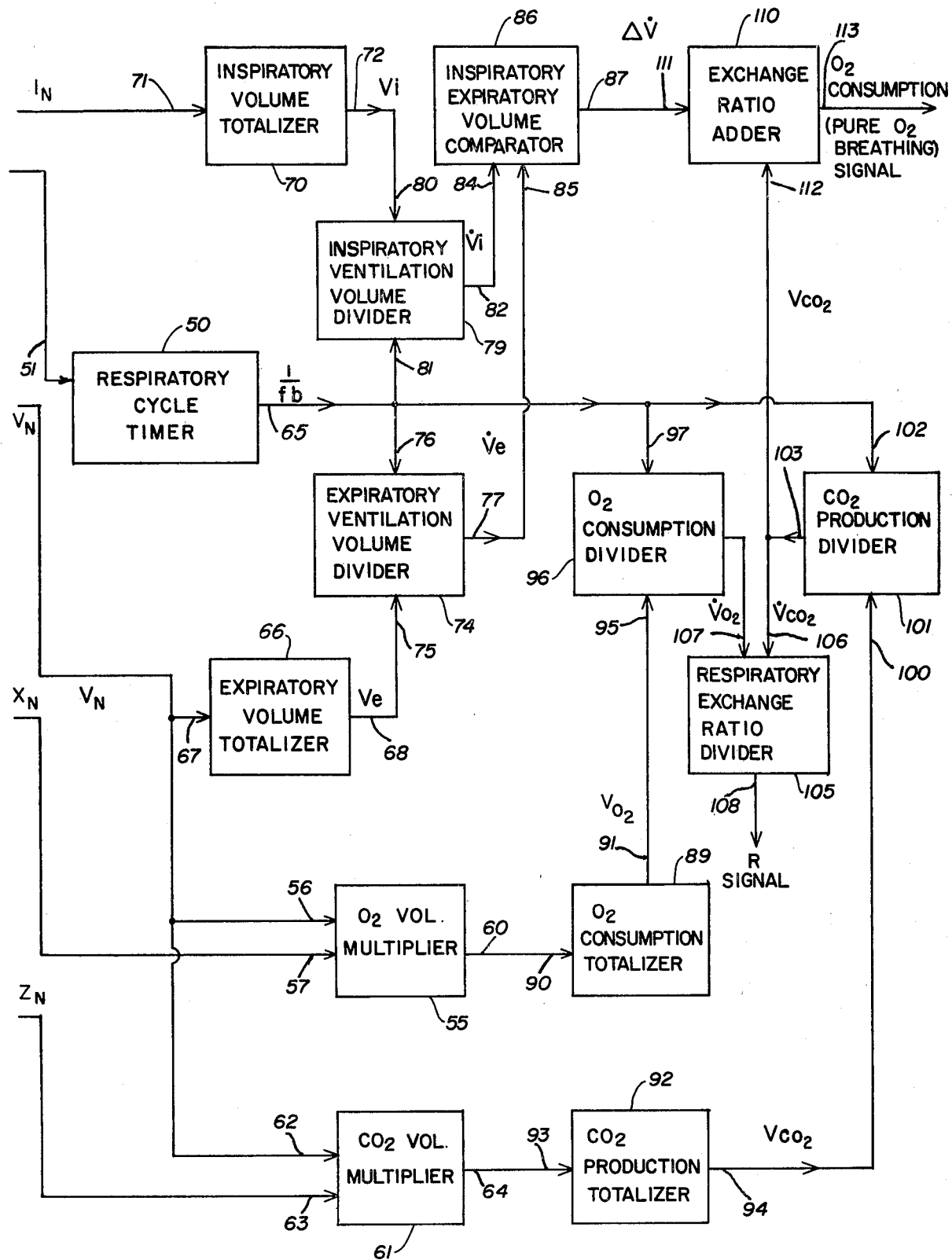
FIG. 2 is a block diagram illustrating principally the computation and display circuitry of the invention, together with cardiotachometer and oximeter.

Referring now to FIG. 1, a bidirectional pneumotach 2 is used to measure inspiratory and expiratory flow rate. The pneumotach has a mouthpiece 3 through which the subject breathes. Inspired and expired air enters and leaves through an opening 4. During conditions of pure oxygen breathing, a demand-regulated oxygen supply is coupled to opening 4. All types of commercially available demand-regulated oxygen supplies are suitable for use with this system including the most commonly available Hudson Valve types. A thin screen 5 is used to provide a slight pressure drop during breathing without imposing noticeable breathing load. A differential pressure transducer 6 senses pressure differential between the two sides of screen 5 and provides two outputs 7 and 8 corresponding to inspired flow and expired flow $dVi/dt$ and $dVe/dt$ respectively. Air from the mouthpiece is drawn through oxygen analyzer 10 and carbon dioxide analyzer 11 by vacuum pump 12. The sampling line 13 is drawn large for purposes of clarity and in reality is of a much smaller diameter relative to the dimensions of the pneumotach. Oxygen analyzer 10 continuously senses the proportion of oxygen in inspired and expired breath and provides an oxygen concentration signal $[O_2]$ at its output 15 proportional thereto. Carbon dioxide analyzer 11 continuously senses the proportion of carbon dioxide in inspired and expired breath and provides a carbon dioxide concentration signal $[CO_2]$ at its output 16 proportional thereto. Differential pressure transducer 6 continuously senses the flow rate of expired breath and provides at its output 8 an expiratory flow signal $dVe/dt$ proportional thereto. Similarly, the flow rate of inspiratory breath is sensed and the differential pressure transducer provides an inspiratory flow signal $dVi/dt$ at its output 7 proportional thereto.

Outputs 7 and 8 from the differential pressure transducer 6 are connected to and processed by inspiratory flow converter 18 and expiratory flow converter 19 respectively. Outputs 15 and 16 from oxygen analyzer 10 and carbon dioxide analyzer 11 are connected to and processed by oxygen signal processor 20 and carbon dioxide signal processor 21 respectively.

In the preferred embodiment, the outputs 7 and 8 from differential pressure transducer 6 are voltages corresponding to inspiratory and expiratory flow rates, respectively. Similarly, the outputs from the gas analyzers 10 and 11 are voltages corresponding to oxygen and carbon dioxide concentrations, respectively. Expiratory flow converter 19 contains within it an expiratory flow integrator 23 having an input 24 connected to output 8 of differential pressure transducer 6 and thus receives expiratory flow signal $dVe/dt$. Expiratory flow integrator 23 is controlled by an expiratory flow activity detector 25 having an input 26 connected to output 8 of differential pressure transducer 6. In the preferred embodiment, activity detector 25 is an electronic circuit which enables expiratory flow integrator 23 upon detecting $dVe>0/dt$ corresponding to the initiation of expiratory flow. Activity detector 25 is configured to reset flow integrator 23 upon the detection of $dVe \leq 0/dt$ corresponding to the completion of expiratory flow. Expiratory flow integrator 23 samples and integrates expiratory flow signal 8 at intervals of t seconds and provides at its output 27 a series of signals $V_0$ through $V_n$ where $V_n$ is proportional to the volume expired during the time elapsed between $t_{n-1}$ and $t_n$.

In the preferred embodiment, the output 15 from oxygen analyzer 10 is connected to an oxygen offset compensator 29. Offset compensator 29 is, in the preferred embodiment, a simple circuit offsetting the voltage which appears at output 15 by a constant amount corresponding to the concentration of oxygen in ambient air. Oxygen offset compensator 29 provides at its output 30 an oxygen differential signal $\Delta[O_2]$ proportional to the instantaneous difference in concentration of oxygen between inhaled and exhaled breath. Oxygen concentration sampler 31 has its input 32 connected to the output 30 of offset compensator 29. The oxygen concentration sampler 31 is controlled by oxygen concentration activity detector 33. Activity detector 33 has an input 34 connected to output 30 and thus receives the same oxygen differential signal received by the sampler 31 which it controls. Oxygen concentration activity detector 33 is a circuit configured to detect a deviation in the oxygen differential signal $\Delta[O_2]$ which corresponds to a drop in detected oxygen concentration below the inspired value. Upon the detection of an oxygen concentration which deviates from the inspired value, activity detector 33 enables sampler 31 which then samples the oxygen differential signal every t seconds and provides at its output 35 a series of signals $X_0$ through $X_n$ proportional to successive instantaneous values in said oxygen differential signal. Resetting of said sampler 31 is accomplished by activity detector 33 when detected oxygen concentration comes back up to inspired level.

Carbon dioxide analyzer 11 continuously senses the proportion of carbon dioxide in inspired and expired breath and provides at its output 16 a carbon dioxide concentration signal $[CO_2]$ proportional thereto. A carbon dioxide offset compensator 35 has its input connected to the output 16 of carbon dioxide analyzer 11. In the preferred embodiment, the output signal from carbon dioxide analyzer 11 is a voltage proportional to carbon dioxide concentration. Offset compensator 35 merely adds or subtracts a voltage to this signal to offset the effect of carbon dioxide concentration in inspired breath. The output 36 of offset compensator 35 is therefore a carbon dioxide differential signal $\Delta[CO_2]$ proportional to the instantaneous difference in concentration of carbon dioxide between inhaled and exhaled breath. A carbon dioxide sampler 38 has its input 39 connected to the output 36 of offset compensator 35 and thus receives the carbon dioxide differential signal $\Delta[CO_2]$. Sampler 38 is controlled by carbon dioxide concentration activity detector 40. The activity detector has its input 41 connected to the output 36 of offset compensator 35 and thus receives the same carbon dioxide differential signal as does the sampler 38 which it controls. In the preferred embodiment, activity detector 40 is an electronic circuit configured so as to enable sampler 38 upon detection of a rise in carbon dioxide concentration above inspired levels. Activity detector 40 resets sampler 38 when the carbon dioxide concentration decreases back down to ambient levels. Carbon dioxide sampler 38 is therefore enabled only when carbon dioxide concentration deviates from the inspired value. Sampler 38, when enabled, samples the carbon dioxide differential signal produced at the output 36 of offset compensator 35 every t seconds and provides at its output 42 a series of signals $Z_0$ through $Z_n$ proportional to successive instantaneous values of the carbon dioxide differential signal. In the preferred embodiment, the offset compensators 29 and 35 effectively remove the influence of inspired concentrations of oxygen and carbon dioxide, respectively, and thus provide at their output a zero voltage when inspired concentrations are sensed by their respective gas analyzers 10 and 11. Any decrease in the oxygen concentration from the inspired value causes a negative voltage to appear at the output of oxygen concentration offset compensator 30. Similarly, any increase in carbon dioxide concentration above inspired levels causes a positive voltage at the output 36 of carbon dioxide concentration offset compensator 35.

Inspired flow converter 18 is configured identically to expired flow converter 19. Differential pressure transducer 6 continuously senses the flow rate of inspired breath and provides at it output 7 an inspired flow signal $dVi/dt$ proportional thereto. Inspiratory flow integrator 45 has its input 46 connected to the output 7 of differential pressure transducer 6 and thus receives inspiratory flow signal $dVi/dt$. Inspiratory flow activity detector 47 has its input 48 connected to output 7 and thus also receives inspiratory flow signal $dVi/dt$. In the preferred embodiment, activity detector 47 is an electronic circuit configured to enable inspiratory flow integrator 45 upon detecting $dVi>0/dt$ corresponding to the onset of inspiratory flow. Inspiratory flow integrator 45 is reset by activity detector 47 upon the detection of $dVi \leq 0/dt$ corresponding to the end of inspiratory breath activity. Integrator 45 samples and integrates inspiratory flow signal $dVi/dt$ at intervals of t seconds and provides at its output 49 a series of signals $I_0$ through $I_n$ where $I_n$ is proportional to the volume inspired during the time elapsed between $t_{n-1}$ and $t_n$.

A respiratory cycle timer 50 receives at its input 51 the enabling signal generated by activity detector 47 upon the detection of the onset of inspiratory flow. Respiratory cycle timer 50 measures the elapsed time between successive enablings of the inspiratory flow integrator 45 and provides at its output 65 a breath duration signal $1/fb$ proportional thereto.

The output of flow integrator 45 is a series of discrete integrated values corresponding to sequential values of inspiratory volume. This sequence is temporarily stored in storage register 53 in order to facilitate later computational manipulations of these values. Similarly the sequential output from expiratory flow integrator 23 is temporarily stored in storage register 24. An oxygen volume multiplier 55 has two multiplying inputs 56 and 57. Input 56 is connected to the output 59 of storage register 54. The signals present at output 59 are simply stored output values from the expiratory flow integrator 23. Input 57 of oxygen volume multiplier 55 is connected to the output 35 of oxygen concentration sampler 31. Oxygen volume multiplier 55 multiplies the corresponding discrete sequential outputs from expiratory flow integrator 23 and oxygen concentration sampler 31, that is $V_n \cdot X_n$ so as to provide at its output 60 a series of signals $V_0 \cdot X_0, \ldots, V_n \cdot X_n$ proportional to the successive incremental values of oxygen uptake within a breath. Similarly, a carbon dioxide volume multiplier 61 is provided and has two multiplying inputs 62 and 63. Input 62 is connected to the output 59 of storage register 54 and thus receives the output signals from expiratory flow integrator 23. Multiplying input 63 is connected to the output 42 of carbon dioxide concentration sampler 38. Carbon dioxide volume multiplier 61 multiplies the corresponding sequential discreet outputs from carbon dioxide concentration sampler 38 and expiratory flow integrator 23 so as to provide at its output 64 a series of signals $V_0 \cdot Z_0, \ldots, V_n \cdot Z_n$ proportional to successive incremental values of carbon dioxide production within a breath.

The output signals of expiratory flow integrator 23 are totalized in expiratory volume totalizer 66 which has its input 67 connected to the output 59 of storage register 54. Totalizer 66 provides at its output 68 a totalized expiratory breath volume signal $\dot{V}_e$ proportional to the sum of $V_0 + \ldots + V_n$. Similarly, the output signals from inspiratory flow integrator 45 are totalized by inspiratory volume totalizer 70 which has its input 71 connected to the output 52 of storage register 54. Totalizer 70 provides at its output 72 a totalized inspiratory breath volume signal Vi proportional to the sum $I_0 + \ldots + I_n$. Expiratory ventilation volume divider 74 is configured with a dividend input 75 connected to output 68 of totalizer 66 so as to receive the totalized expiratory volume signal Ve. Expiratory ventilation volume divider 74 has a divisor input 76 connected to the output 52 of respiratory cycles timer 50 and thus receives the breath duration signal 1/fb. Expiratory ventilation volume divider 74 provides at its output 77 a quotient signal $\dot{V}_e$ proportional to the expired breath volume per unit time. Similarly, inspiratory ventilation volume divider 79 is configured with a dividend input 80 connected to the output 72 of inspiratory totalizer 70 so as to receive the totalized inspiratory volume signal Vi. Inspiratory ventilation volume divider 79 has a divisor input 81 connected to the output 52 of respiratory cycle timer 50 so as to receive the breath duration signal 1/fb. Inspiratory ventilation volume divider 70 provides at its output a quotient signal Vi proportional to the inspiratory breath volume per unit time. The outputs from both the inspiratory ventilation divider 79 and the expiratory ventilation volume divider 74 are connected to the two comparing inputs 84 and 85 of inspiratory-expiratory ventilation volume comparator 86. Comparator 86 compares the signals present at its inputs and provides at its output 87 an inspiratory-expiratory breath volume differential signal $\Delta \dot{V}$ proportional to the difference between inspired and expired breath volume per unit time.

Oxygen consumption totalizer 89 has its input 90 connected to the output 60 of oxygen volume multiplier 55 and provides at its own output 91 a totalized oxygen volume signal $\dot{V}_{O2}$ proportional to the sum $V_0 \cdot X_0 + \ldots + V_n \cdot X_n$. Similarly, carbon dioxide production totalizer 92 has its input 93 connected to the output 64 of carbon dioxide volume multiplier 61 and provides at its own output 94 a totalized carbon dioxide production signal $V_{CO2}$ proportional to the sum $V_0 \cdot Z_0 + \ldots + V_0 \cdot Z_n$. The output 91 of oxygen consumption totalizer 89 is connected to the dividend input 95 of oxygen consumption divider 96. The divisor input 97 of oxygen consumption divider 96 is connected to the output 52 of respiratory cycle timer 50 so as to receive the breath duration signal 1/fb. Oxygen consumption divider 96 provides at its output 98 a quotient signal $V_{O2}$ proportional to the rate of oxygen consumption. The output 94 of carbon dioxide production totalizer 92 is connected to the dividend input 100 of carbon dioxide production divider 101. The divisor input 102 of divider 101 is connected to the output 52 of respiratory cycle timer 50 so as to receive the breath duration signal 1/fb. Carbon dioxide production divider 100 provides at its output 103 a quotient signal $\dot{V}_{CO2}$ proportional to the rate of carbon dioxide production.

Respiratory exchange ratio divider 105 has its dividend input 106 connected to the output 103 of carbon dioxide production divider 101 and its divisor input 107 connected to the output 98 of oxygen consumption divider 96. Respiratory exchange ratio divider 105 provides at its output 108 a signal R proportional to the ratio of carbon dioxide produced to oxygen consumed. The output from divider 105 is the respiratory exchange ratio R which has great physiologic significance. The onset of anaerobic metabolism, for example, corresponds to values of R equal to or greater than 1.

The two standard protocols for exercise testing involve normal air breathing and pure oxygen breathing. In the instant invention oxygen consumption during conditions of pure oxygen breathing can be continuously monitored since the volume of inspired as well as expired gas is measured. Under conditions of pure oxygen breathing, the difference between inhaled and exhaled breath volume $\Delta \dot{V}$ is equal to the difference between oxygen uptake and carbon dioxide production ($\dot{V}_{O2} - \dot{V}_{CO2}$). Stated algebraically, $\Delta \dot{V} = \dot{V}_{O2} - \dot{V}_{CO2}$ or $\dot{V}_{O2} = \Delta \dot{V} + \dot{V}_{CO2}$. The instant invention provides a simple and structurally novel means to measure $\dot{V}_{O2}$ during conditions of pure oxygen breathing. Exchange ratio adder 110 has two adding inputs 111 and 112. 111 is connected to the output 87 of inspiratory-expiratory ventilation volume comparator 86 and input 112 is connected to the output 103 of carbon dioxide production divider 101. During conditions of pure oxygen breathing, the signal produced at the output 113 of exchange ratio 110 is proportional to oxygen consumption per unit time.

Figure 5:
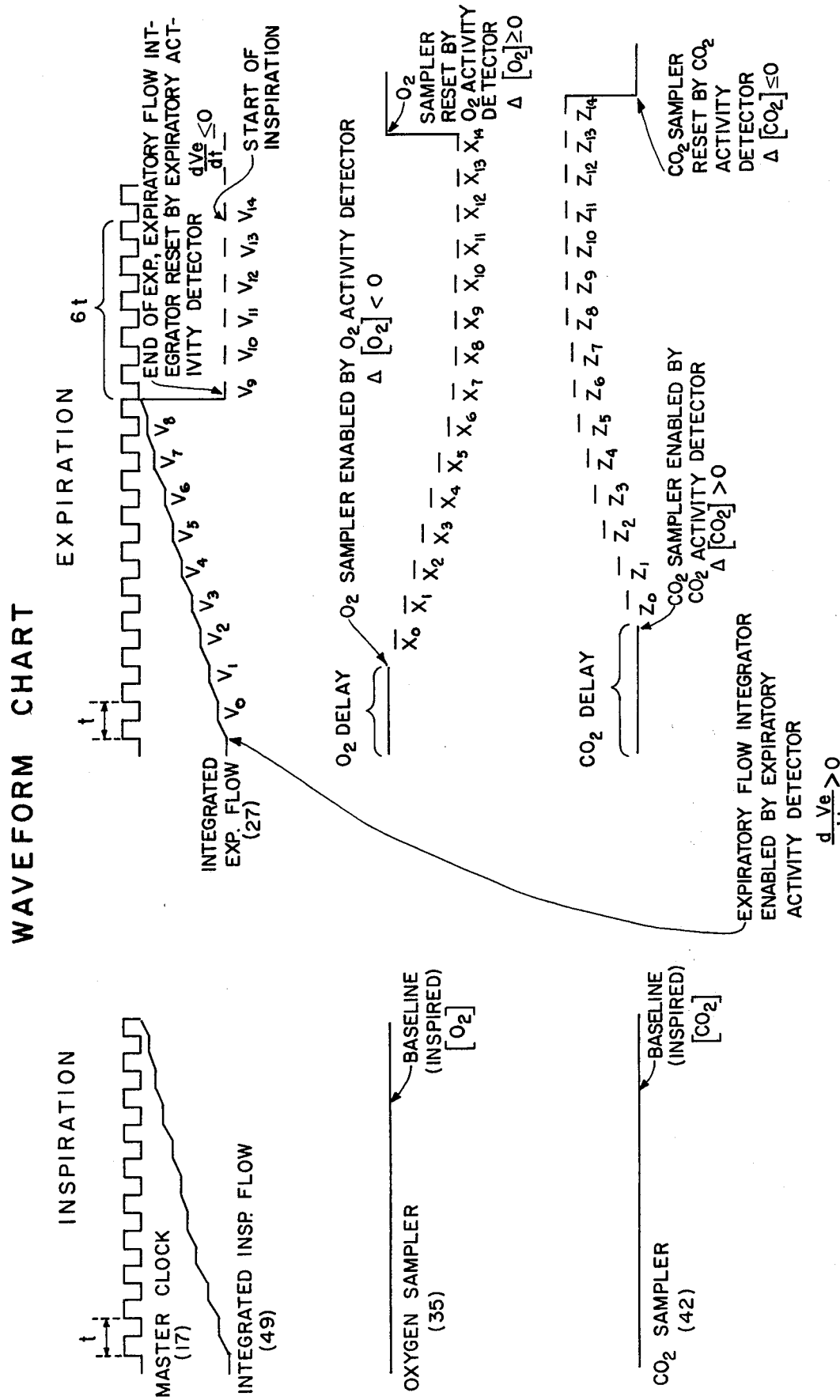

The novel features of the instant invention are found primarily, but not exclusively, within the blocks of flow convertors 18 and 19 and gas concentration signal processors 20 and 21. The downstream hardware such as the various totalizers and dividers could be equivalently implemented in software. In the preferred embodiment, the sampling rate of the two integrators 23 and 45 and the two gas concentration samplers 31 and 38 are all controlled by a master sampling clock so that an identical sampling rate is obtained. In the preferred embodiment, a master clock resides within digital processor 116 and provides a master clock output 117. This master clock output is connected to the clock inputs (labeled "t") of inspired flow integrator 45, expired flow integrator 23, oxygen sampler 31, and carbon dioxide sampler 38. FIG. 5 is a waveform chart illustrating integrator and sampler outputs during inspiration and expiration. Inspiration is portrayed on the left-hand portion of the chart and expiration on the right-hand portion. The top line illustrates the output 17 of the master clock. The master clock determines the sampling and integrating rate for the flow converters and the gas signal processors. Examining now the lefthand portion of FIG. 5, it is seen that the output 35 of oxygen sampler 31 remains at a zero level. This is due to the fact that during inspiration the activity detector 33 does not enable the oxygen sampler since the concentration of oxygen detected corresponds to the inspired level. Similarly, the output 42 of carbon dioxide sampler is zero during the illustrated portion of inhalation since the carbon dioxide activity detector 40 detects a carbon dioxide concentration corresponding to the inspired level and therefore does not enable the sampler. The right-hand portion of FIG. 5 represents a simplified graphic illustration of the waveforms obtained during and after expiration. To illustrate the versatility of the instant invention, different delay periods are shown for the enabling of the oxygen sampler and the carbon dioxide sampler. As will be seen, these delays do not affect the ultimate accuracy of the system.

As can be seen by examining FIG. 5, the expiratory flow integrator is enabled by its respective activity detector prior to the enabling of the oxygen sampler which is in turn followed by the enabling of the carbon dioxide sampler. The first integrated value of expiratory flow following enabling of the expiratory flow integrator 23 by its activity detector 25 results in a value of expiratory volume labeled $V_0$. The following values are labeled $V_1$ through $V_8$ where $V_n$ is proportional to the time elapsed between $t_{n-1}$ and $t_n$. The first sampled value of oxygen concentration following the enabling of oxygen sampler 31 by its activity detector 33 is labeled $X_0$. Successive sampled values are labeled $X_1$ through $X_{14}$ and are proportional to successive instantaneous sampled values of oxygen concentration. The first sampled value of carbon dioxide concentration following the enabling of carbon dioxide sampler 38 by its activity detector 40 is labeled $Z_0$. Successive instantaneous sample values of carbon dioxide concentration are labeled $Z_1$ through $Z_{14}$. Although $V_0$, $X_0$ and $Z_0$ appear at the outputs of their respective integrators and samplers at different times, they all correspond to each other in that the first value sampled by the oxygen sampler ($X_0$) corresponds to the first carbon dioxide sample ($Z_0$) and the first sample value of expiratory volume ($V_0$). Even though these values of volume and gas concentration are obtained at slightly different times, owing to sensor response lags, plumbing delays, etc., once obtained they can be multiplied, divided and otherwise computationally processed as synchronized signals. As a result of this unique configuration of samplers and integrators, each controlled by its own activity detector, a series of discrete volume and gas concentration signals are obtained which can be used in computations as soon as the first values are obtained.

Referring to the right-hand portion of FIG. 5, it should be noted that expiration ceases after $V_8$ and the onset of inhalation occurs at $V_{14}$ after a delay of 6t. There is a plateau value of [O2] (seen as $X_9$ through $X_{14}$) and a plateau value of [CO2] (seen as $Z_9$ through $Z_{14}$). These plateaus are due to the fact that the oxygen and carbon dioxide samplers continue, after the end of expiration, to sample the stagnant gas remaining in the system plumbing (deadspace). These samples are reset only after inspiration begins and their activity detectors sense inspired gas concentration values. This is illustrated at the far right-hand portion of FIG. 5.

The aforementioned deadspace sampling does not introduce any error whatsoever into the system. The expiratory flow is not affected by deadspace, and the output of the expiratory flow integrator is reset to zero at the end of expiration. The calculated volume of carbon dioxide produced, $V_{CO2}$, and oxygen consumed, $V_{O2}$, during the time elapsed after the end of expiration is zero since $$V_9 \cdot X_9 + \ldots + V_{14} \cdot X_{14} = 0 \text{ and}$$

$$V_9 \cdot Z_9 + \ldots + V_{14} \cdot Z_{14} = 0.$$

System versatility is further enhanced by the inclusion of peak detectors within the flow converters and gas concentration signal processors. Peak detector 120, located within an inspired flow converter 18, detects and stores the peak value of the inspiratory flow signal which is then made available at its output. Peak detector 121 located within expired flow converter 19 performs a similar function for the peak expiratory flow signal. Peak detector 122, located within the oxygen signal processor 20, detects the minimum value of oxygen concentration. Peak detector 123 located within the carbon dioxide signal processor 21 detects the maximum value of carbon dioxide concentration. The minimum oxygen concentration and maximum carbon dioxide concentration are available at the output of peak detectors 122 and 123, respectively, and correspond to the end tidal or alveolar oxygen and carbon dioxide concentrations.

Figure 3:
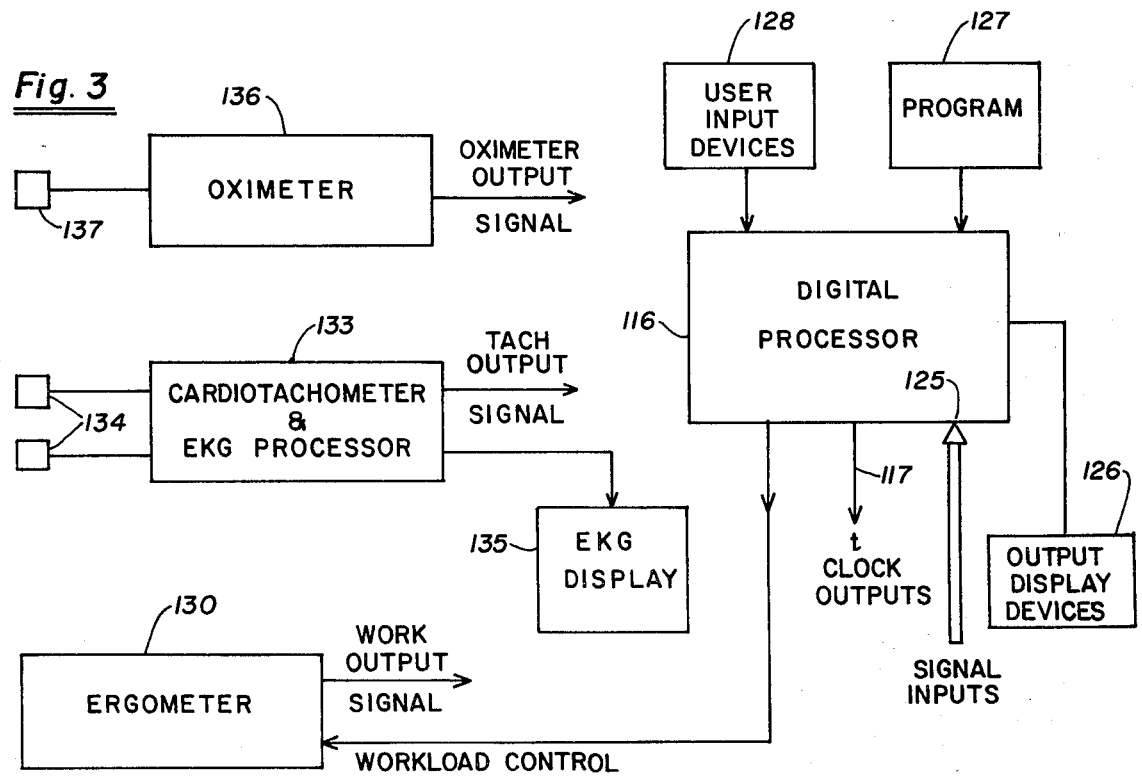
FIG. 3 is a waveform chart illustrating sampler and integrator outputs during inspiration and expiration. example of a graphical output from the system.

Digital processor 116, shown in FIG. 3, receives at its signal input port 125 the various signal outputs produced by the apparatus depicted in FIG. 1. In the preferred embodiment, digital processor 116 is a programmable microprocessor. Output display devices 126 include meters, printers, CRT graphic displays, plotters, and the like. Program 127 can reside in ROM, disc, or other storage medium and is used to control the microprocessor in its various computational, timing, and related functions. User input devices 128 include keyboards and the like for inputting data concerning the test subject and for inputting on-line control commands to the processor 116. Ergometer 130 is, in the preferred embodiment, a variable load treadmill or bicycle upon which the subject works while undergoing physiologic analysis. A workload control input is shown in FIG. 3 so that workload can be varied by the digital processor. This could be useful in certain research situations and also provides an added safety feature in that workload could be reduced upon the detection of any cardiac or respiratory conditions indicative of excessive stress. The work output signal from ergometer 130 is connected to signal input port 125 of digital processor 116. The work output signal can be displayed on one of the various output display devices 126 to aid the subject in maintaining a constant work output should this be necessary for testing. Cardiotachometer and EKG processor 133 is shown with its electrode inputs 134 displayed on the left-hand portion of the diagram. Although only a pair of leads are shown, any number may be used according to the type of EKG processor employed. The cardiotach output signal 133 is connected to the signal input port 125 and is processed with the other signal inputs. One of the important features of the instant invention is that the results of the tests can be displayed in a highly meaningful fashion by displaying heart rate and other physiologic variables as a function of measured, rather than assumed or estimated, oxygen consumption. EKG display 135 is typically a separate CRT and/or a strip chart recorder used to display the waveform of the electrical activity of the subject's heart.

Figure 4:
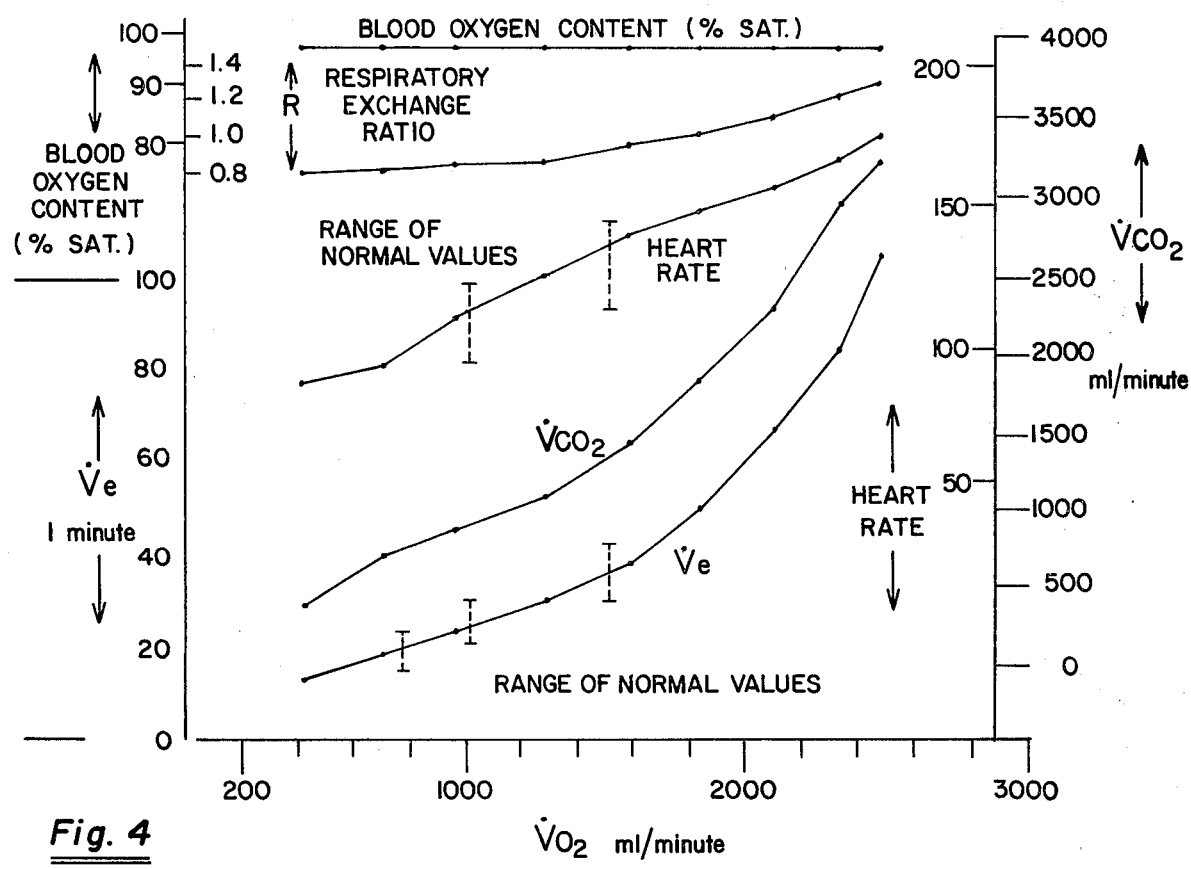
FIG. 4 is an example of a graphical output from the system.

Oximeter 136 is used to measure the actual oxygen content in the subject's blood. In the preferred embodiment, oximeter 136 employs a non-invasive transducer 138 unit. The output of oximeter 136 is connected to the signal input port 125 of digital processor 116. The usefulness of computing and displaying the various physiologic variables as a function of measured oxygen consumption rather than time is clearly illustrated in FIG. 4.

One very important advantage offered by the instant invention is that highly useful metabolic data can be obtained from extremely short exercise periods. Since computations of oxygen uptake and carbon dioxide production can begin as soon as the first values ($V_0$, $X_0$, $Z_0$) are obtained, the subject need not be exercised for long periods on the ergometer in order to obtain useful metabolic data. Often, in the case of seriously ill patients, useful tests, such as those performed by the instant invention, are foregone since the patient is unable to sustain prolonged exercise. Another advantage attendant to the structure of the instant invention is that coughs, short breaths, and erratic breathing patterns do not give wildly inaccurate or erratic metabolic data since the initiation of sampling and integration is controlled by activity detectors which respond to actual physiologic occurences and do not depend upon a preconceived notion of "normal" timing or breath patterns.

What is claimed is:

1. A physiologic analyzer comprising:
means continuously sensing the flow rate of expired breath and providing an expired flow signal proportional thereto;
means continuously sensing the proportion of oxygen in inspired and expired breath and providing an oxygen concentration signal proportional thereto;
means continuously sensing the proportion of carbon dioxide in inspired and expired breath and providing a carbon dioxide concentration signal proportional thereto;
an expiratory flow integrator enabled only during expiratory breath and having its input connected to said expiratory flow signal and which samples and integrates said expiratory flow signal at intervals of t seconds and provides at its output a series of signals $V_0$ through $V_n$ where $V_n$ is proportional to the volume expired during the time elapsed between $t_{n-1}$ and $t_n$;
an expiratory oxygen concentration sampler which is enabled only when oxygen concentration deviates from the inspired value and which samples oxygen concentration every t seconds and provides at its output a series of signals $X_0$ through $X_n$ proportional to successive instantaneous values of said oxygen concentration;
an expiratory carbon dioxide concentration sampler which is enabled only when carbon dioxide concentration deviates from the inspired value and which samples carbon dioxide concentration every t seconds and provides at its output a series of signals $Z_0$ through $Z_n$ proportional to successive instantaneous values of said carbon dioxide concentrations.

2. The device of claim 1 further comprising:
means continuously sensing the flow rate of inspired breath and providing an inspired flow signal proportional thereto;
a respiratory cycle timer having its input connected to said inspiratory flow signal, said timer measuring the time elapsed between successive inspirations and providing at its output a breath duration signal proportional thereto;
an oxygen volume multiplier having two multiplying inputs, one of said inputs connected to the output of said expiratory flow integrator and the other of said inputs connected to the output of said oxygen concentration sampler, said oxygen volume multiplier multiplying $V_n \cdot X_n$ to provide at its output a series of signals $V_0 \cdot X_0, \ldots, V_n \cdot X_n$ proportional to the successive incremental values of oxygen uptake within a breath;
a carbon dioxide volume multiplier having two multiplying inputs, one of said inputs connected to the output of said expiratory flow integrator and the other of said inputs connected to the output of said carbon dioxide concentration sampler, said carbon dioxide volume multiplier multiplying $V_n \cdot Z_n$ to provide at its output a series of signals $V_0 \cdot Z_0, \ldots, V_n \cdot Z_n$ proportional to successive incremental values of carbon dioxide production within a breath.

3. The device of claim 2 further comprising:
an oxygen consumption totalizer having its input connected to the output of said oxygen volume multiplier and providing at its output a totalized oxygen volume signal proportional to the sum $V_0 \cdot X_0 + \ldots + V_n \cdot X_n$;
an oxygen consumption divider having a divident input connected to said totalized oxygen volume signal and a divisor input connected to said breath duration signal and providing at its output a quotient signal proportional to the rate of oxygen uptake;
a carbon dioxide production totalizer having its input connected to the output of said carbon dioxide volume multiplier and providing at its output a totalized carbon dioxide production signal proportional to the sum $V_0 \cdot Z_0 + \ldots + V_n \cdot Z_n$;
a carbon dioxide production divider having a dividend input connected to said carbon dioxide totalizer and a divisor input connected to said breath duration signal and providing at its output a quotient signal proportional to the rate of carbon dioxide production.

4. The device of claim 3 further comprising:
a respiratory exchange ratio divider having its dividend input connected to the output of said carbon dioxide production divider and a divisor input connected to the output of said oxygen consumption divider and providing at its output a signal proportional to the ratio of carbon dioxide produced to oxygen consumed.

5. The device of claim 4 further comprising:
an inspiratory flow integrator enabled only during inspiratory breath and having its input connected to said inspiratory flow signal and which samples and integrates said inspiratory flow signal at intervals of t seconds and provides at its output a series of signal $I_0 \ldots I_n$ where $I_n$ is proportional to the volume inspired during the time elapsed between $t_{n-1}$ and $t_n$;
an expiratory volume totalizer having its input connected to the output of said expiratory flow integrator and providing at its output a totalized expiratory breath volume signal proportional to the sum of $V_0 + \ldots + V_n$;
an expiratory ventilation volume divider having a dividend input connected to said totalized expiratory volume signal and a divisor input connected to said breath duration signal and providing at its output a quotient signal proportional to the expired breath volume per unit of time;
an inspiratory volume totalizer having its input connected to the output of said inspiratory flow integrator and providing at its output a totalized inspiratory breath volume signal proportional to the sum $I_0 + \ldots I_n$;
an inspiratory ventilation volume divider having a divident input connected to said totalized inspiratory volume signal and a divisor input connected to said breath duration signal and providing at its output a quotient signal proportional to the inspiratory volume of breath per unit time;

an inspiratory-expiratory ventilation volume comparator having two comparing inputs, one connected to the output of said inspiratory breath volume divider and the other connected to the output of said expiratory breath volume divider and providing at its output an inspiratory-expiratory breath volume differential signal proportional to the difference between inspired and expired breath volume;

an exchange ratio adder having two adding inputs, one connected to the output of said inspiratory-expiratory ventilation volume comparator and the other input connected to the output of said carbon dioxide production divider providing at its output, during conditions of pure oxygen breathing, a signal proportional to the oxygen consumption per unit time.

6. The device of claim 3 further comprising:

a processor responsive to the output signals of said expiratory ventilation volume divider, said oxygen consumption divider, and said carbon dioxide production divider, said processor converting said output signals into actual values for the volume of expiratory ventilation, carbon dioxide production rate, and oxygen consumption rate.

7. The device of claim 6 further comprising:

display means connected to said processor and driven thereby for graphically displaying both expiratory flow rate and carbon dioxide production rate as a function of oxygen consumption rate.

8. The device of claim 7 further comprising:

a cardiotachometer having an output signal proportional to heart rate;

said processor further responsive to said cardiotachometer output signal and converting said output signal into actual values for heart rate;

said display means further graphically displaying heart rate as a function of oxygen consumption rate.

9. The device of claim 8 further comprising:

an oximeter having an output signal proportional to the oxygen content of arterial blood;

said processor further responsive to said oximeter output signal and converting said signal into actual values for arterial blood oxygen content;

said display means further graphically displaying arterial blood oxygen content as a function of oxygen consumption rate.

10. In a physiologic analyzer having means continuously sensing the flow rate of expired breath, means continuously sensing the concentration of oxygen in inspired and expired breath, and means continuously sensing the concentration of carbon dioxide in inspired and expired breath, the method comprising:

sampling and integrating the expiratory flow rate at intervals of t seconds to provide a series of values of expiratory volume $V_0$ through $V_n$ where $V_n$ is the volume expired during the time elapsed between $t_{n-1}$ and $t_n$;

sampling, upon detecting oxygen concentration which deviates from the inspired value, the oxygen concentration every t seconds to provide a series of oxygen concentration values $X_0$ through $X_n$ proportional to successive instantaneous values of expired oxygen concentration;

sampling, upon detecting carbon dioxide concentration which deviates from the inspired value, the carbon dioxide concentration every t seconds to provide a series of carbon dioxide concentration value $Z_0$ through $Z_n$ proportional to successive instantaneous values of carbon dioxide concentration in expired breath.

11. The method of the previous claim further comprising multiplying $V_n \cdot X_n$ to provide a series $V_0 \cdot X_0, \ldots, V_n \cdot X_n$ proportional to the successive incremental values of oxygen consumption within a breath;

multiplying $V_n \cdot Z_n$ to provide a series of values $V_0 \cdot Z_0, \ldots, V_n \cdot Z_n$ proportional to successive incremental values of carbon dioxide production within a breath.

* * * * *